United States Patent
James et al.

(10) Patent No.: US 10,716,784 B2
(45) Date of Patent: *Jul. 21, 2020

(54) PAIN MEDICINE COMBINATION AND USES THEREOF

(71) Applicant: MindLab LLC, New York, NY (US)

(72) Inventors: Lawrence R. James, New York, NY (US); Laura A. James, New York, NY (US)

(73) Assignee: MINDLAB LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/201,129

(22) Filed: Mar. 7, 2014

(65) Prior Publication Data

US 2014/0256763 A1    Sep. 11, 2014

Related U.S. Application Data

(60) Provisional application No. 61/774,113, filed on Mar. 7, 2013.

(51) Int. Cl.
*A61K 31/485* (2006.01)
*A61K 31/4709* (2006.01)
*A61K 31/49* (2006.01)

(52) U.S. Cl.
CPC ........ *A61K 31/485* (2013.01); *A61K 31/4709* (2013.01); *A61K 31/49* (2013.01)

(58) Field of Classification Search
CPC .......................... A61K 31/485; A61K 31/4709
USPC ........................................................ 514/282
See application file for complete search history.

(56) References Cited

U.S. PATENT DOCUMENTS

| | | | |
|---|---|---|---|
| 5,698,155 A | 12/1997 | Grosswald et al. | |
| 6,136,839 A | 10/2000 | Isakson et al. | |
| 6,207,674 B1* | 3/2001 | Smith .................. | A61K 31/135 514/289 |
| RE38,115 E | 5/2003 | Smith et al. | |
| 8,231,901 B2 | 7/2012 | Breder et al. | |
| 2007/0196481 A1 | 8/2007 | Amidon et al. | |
| 2009/0111846 A1 | 4/2009 | Berg | |
| 2010/0196269 A1 | 8/2010 | Dolle et al. | |
| 2010/0249045 A1* | 9/2010 | Babul .................... | A61K 9/485 514/21.4 |
| 2012/0165363 A1 | 6/2012 | Yakatan et al. | |
| 2012/0172388 A1 | 7/2012 | Smith | |
| 2012/0231092 A1 | 9/2012 | Oronsky et al. | |
| 2016/0030417 A1 | 2/2016 | James et al. | |

FOREIGN PATENT DOCUMENTS

| | | |
|---|---|---|
| EP | 1535615 A1 | 6/2005 |
| JP | 2004-043479 A | 2/2004 |
| JP | 2005/306882 A | 11/2005 |
| JP | 2012/116858 A | 6/2012 |
| JP | 2012/131815 A | 7/2012 |
| WO | 9848821 A2 | 11/1998 |
| WO | 2004006930 A1 | 1/2004 |

OTHER PUBLICATIONS

Morphine Dosages Retrieved from: Drugs.com [Retrieved on: Aug. 19, 2015] [May 2, 2010] <url:https://web.archive.org/web/20100502161713/http://www.drugs.com/dosage/morphine.html>.*
Leavitt. Opioid ANtagonist in Pain Management. PPM Apr. 1, 2009, pp. 1-6.*
Bell Combine and conquer: advantages and disadvantages of fixed-dose combination therapy(Diabetes, Obesity and Metabolism (2013), vol. 15, pp. 291-300; Published Online Oct. 2012).*
Samer et al., "The effects of CYP2D6 and CYP3A activities on the pharmacokinetics of immediate release oxycodone," British Journal of Pharmacology (2010) 160:907-918.
Samer et al., "Genetic polymorphisms and drug interactions modulating CYP2D6 and CYP3A activities have a major effect on oxycodone analgesic efficacy and safety," British Journal of Pharmacology (2010) 160:919-930.
Akerele et al., "Dextromethorphan and Quinidine Combination for Heroin Detoxification" Am J. Addict (2008), vol. 17, pp. 176-180.
European Search Report dated Nov. 11, 2016 in EP Application No. 14760959.8.
Galer, "MorphiDex® (morphine sulfate/dextromethorphan hydrobromide combination) in the treatment of chronic pain: Three multicenter, randomized, double-blind, controlled clinical trials fail to demonstrate enhanced opioid analgesia or reduction in tolerance" Pain 115 (2005) pp. 284-295.
Mercadante et al., Analgesic effect of intravenous ketamine in cancer patients on morphine therapy, Journal of Pain of Symptom Management 2000 20(4):246-252.
Weinbroum et al., Dextromethorphan for the reduction of immediate and late postoperative pain and morphine consumption in orthopedic oncology patients, Cancer 2002 95(5):1164-1170.
Final Office Action in U.S. Appl. No. 14/772,128 dated Nov. 15, 2017.
PubChem CID 5462351 [online] Retrieved on Nov. 6, 2017 Retrieved from Internet url:https://pubchem.ncbi.nlm.nih.gov/compound/Dextromethorphan_hydrobromide_monohydrate, (2016).

* cited by examiner

*Primary Examiner* — Taina D Matos Negron
(74) *Attorney, Agent, or Firm* — Pepper Hamilton LLP

(57) ABSTRACT

This application describes compounds, compositions, pharmaceutical compositions that can be used in the treatment of, for example, pain and pain related disorders.

20 Claims, No Drawings

PAIN MEDICINE COMBINATION AND USES THEREOF

CROSS REFERENCE TO RELATED APPLICATIONS

This application claims priority to U.S. Provisional Application No. 61/774,113 filed Mar. 7, 2013, which is hereby incorporated by reference in its entirety.

FIELD OF THE INVENTION

Embodiments described herein relate to compositions and pharmaceutical compositions that can be used to treat or prevent pain.

BACKGROUND

Pain is the most common symptom for which patients seek medical advice and treatment. Pain can be acute or chronic. While acute pain is usually self-limited, chronic pain, which can persist for 3 months or longer and can lead to significant changes in a patient's personality, lifestyle, functional ability and overall quality of life. Pain is often treated opioid agonists, such as morphine, oxycodone and hydromorphone. Unfortunately, opioid agonists can have severe side effects that limit their use and effectiveness as treating and/or preventing pain. Therefore, the embodiments described herein provide for compositions that can be used to treat and/or prevent pain with significant and unexpected advantages over compositions currently used to treat or prevent pain.

SUMMARY OF THE INVENTION

Embodiments described herein provide pharmaceutical compositions comprising dextromethorphan, or a pharmaceutically acceptable salt thereof; quinidine, or a pharmaceutically acceptable salt thereof; and an opioid agonist chosen from one or more of: morphine, oxycodone, and hydromorphone, or a pharmaceutically acceptable salt thereof, or any combination thereof. In some embodiments, the compositions is formulated for simultaneous administration. In some embodiments, the ratio of the opioid agonist to dextromethorphan is about 1:1 (wt:wt). In some embodiments, the ratio of the opioid agonist to quinidine is about 1:0.1 to 1:1 (wt:wt). In some embodiments, the ratio of the opioid agonist to dextromethorphan to quinidine is 1:1:0.1-1 (wt:wt:wt). In some embodiments, the composition comprises about 10 mg, about 20 mg, about 30 mg, about 40 mg, about 50 mg, or about 60 mg of the opioid agonist.

Embodiments described herein provide dosage forms comprising dextromethorphan, or a pharmaceutically acceptable salt thereof quinidine, or a pharmaceutically acceptable salt thereof and an opioid agonist chosen from one or more of: morphine, oxycodone, and hydromorphone, or a pharmaceutically acceptable salt thereof, or any combination thereof. In some embodiments, the composition comprises about 10 mg, about 20 mg, about 30 mg, about 40 mg, about 50 mg, or about 60 mg of the opioid agonist.

Methods of treating or preventing pain in a subject are also provided. In some embodiments, the method comprises administering to the subject a pharmaceutical composition described herein. In some embodiments, the pharmaceutical composition is administered every 4 hours, every 6 hours, every 8 hours, or every 12 hours. In some embodiments, the method does not comprise a risk evaluation mitigation strategy (REMS). In some embodiments, the subject is a subject in need of pain relief. In some embodiments, none of the components are administered for the purpose of avoiding withdrawal symptoms.

DETAILED DESCRIPTION

Unless otherwise defined, all technical and scientific terms used herein have the same meaning as commonly understood by one of ordinary skill in the art. Although methods and materials similar or equivalent to those described herein can be used in the practice or testing of the compositions and compounds described herein, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the compositions and compounds described herein will be apparent from the following detailed description and claims.

Various compositions are described herein. Each of the compositions described herein can also be pharmaceutical compositions.

The present invention provides compositions that unexpectedly and surprisingly are treat or prevent pain with a lower amount of an opioid agonist and with fewer side effects will providing improved pain relief or analgesia. The compositions treat or prevent pain relief better than with just the opioid agonist alone. Additionally, the compositions increase the bioavailability of the opioid agonist to the brain. Without being bound to any particular theory, it is the increase in bioavailability that allows a smaller amount of the opioid agonist to be used and to still be able to treat or prevent pain. The compositions also surprisingly and unexpectedly will have an effect that is longer in duration than the opioid agonist alone. The compositions also surprisingly and unexpectedly have a lower incidence of tolerance. That is, under certain circumstances increasing amounts of the opioid agonist are necessary to achieve the same level of pain relief. For the compositions described herein, the compositions will have a lower incidence of tolerance, thereby keeping the amount of the opioid agonist to a minimum, which reduces the adverse side effects that are common to the usage of opioid agonists. The advantages described herein apply to having all three components (e.g. opioid antagonist, dextromethorphan and quinidine) administered or present in a composition as opposed to just two of an opioid agonist, dextromethorphan or quinidine. In some embodiments, the combination of an opioid agonist, dextromethorphan and quinidine has other reduced side effects as compared to any of the components alone or a combination of two of them. Examples of morphine side effects include, but are not limited to, weight loss constipation, diarrhea, nausea, vomiting, stomach pain, loss of appetite, flushing (e.g. warmth, redness, or tingly feeling), headache, dizziness, spinning sensation, memory problems, sleep problems (insomnia), or strange dreams. Therefore, the compositions described herein can reduce or lessen the side effects.

In some embodiments, a composition comprising an opioid agonist, dextromethorphan, quinidine, pharmaceutically acceptable salt of each or any of the foregoing, or any combination thereof. Examples of opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts of each or any of the foregoing, and any mixtures thereof. In some embodiments, the opioid agonist is morphine, oxycodone, and hydromorphone, or a pharmaceutically acceptable salt thereof, or any combination thereof. In some embodiments, the morphine is morphine sulfate.

In some embodiments, the composition is formulated for simultaneous administration. As used herein "simultaneous administration," as it refers to a composition comprising more than one active ingredient or therapeutic agent, means that each of the active ingredients or therapeutic agents are administered substantially or exactly at the same time. The agents may be absorbed or become bioavailable at different rates or times, but the administration of the components, ingredients, or agents, is simultaneous. In some embodiments, the administration is not simultaneous.

The ratio of the different components present in the composition can also be altered. In some embodiments, the ratio of the opioid agonist to dextromethorphan is about 1:1 (wt:wt). In some embodiments, the ratio of the opioid agonist to dextromethorphan is about 0.1 to 1:1 (wt:wt). In some embodiments, the ratio of the opioid agonist to dextromethorphan is about 0.5 to 1:1 (wt:wt). In some embodiments, the ratio of the opioid agonist to dextromethorphan is about 0.7 to 1:1 (wt:wt). In some embodiments, the ratio of the opioid agonist to dextromethorphan is about 0.8 to 1:1 (wt:wt). In some embodiments, the ratio of the opioid agonist to dextromethorphan is about 0.9 to 1:1 (wt:wt). In some embodiments, the ratio of the opioid agonist to quinidine is about 1:0.1 to 1:1 (wt:wt). In some embodiments, the ratio of the opioid agonist to quinidine is about 1:0.2 to 1:1 (wt:wt). In some embodiments, the ratio of the opioid agonist to quinidine is about 1:0.3 to 1:1 (wt:wt). In some embodiments, the ratio of the opioid agonist to quinidine is about 1:0.4 to 1:1 (wt:wt). In some embodiments, the ratio of the opioid agonist to quinidine is about 1:0.5 to 1:1 (wt:wt). In some embodiments, the ratio of the opioid agonist to quinidine is about 1:0.6 to 1:1 (wt:wt). In some embodiments, the ratio of the opioid agonist to quinidine is about 1:0.7 to 1:1 (wt:wt). In some embodiments, the ratio of the opioid agonist to quinidine is about 1:0.8 to 1:1 (wt:wt). In some embodiments, the ratio of the opioid agonist to quinidine is about 1:0.9 to 1:1 (wt:wt). In some embodiments, the ratio of the opioid agonist to dextromethorphan to quinidine is 1:1:0.1-1 (wt:wt:wt).

In some embodiments, the composition comprises about 10 mg, about 20 mg, about 30 mg, about 40 mg, about 50 mg, about 60 mg of the opioid agonist. In some embodiments, the composition comprises from about 10 to about 100 mg, from about 10 to about 90 mg, from about 10 to about 80 mg, from about 10 to about 70 mg, from about 10 to about 60 mg, from about 10 to about 50 mg, from about 10 to about 40 mg, from about 10 to about 30 mg, from about 10 to about 20 mg, from about 20 to about 100 mg, from about 20 to about 90 mg, from about 20 to about 80 mg, from about 20 to about 70 mg, from about 20 to about 60 mg, from about 20 to about 50 mg, from about 20 to about 40 mg, from about 20 to about 30 mg, from about 30 to about 100 mg, from about 30 to about 90 mg, from about 30 to about 80 mg, from about 30 to about 70 mg, from about 30 to about 60 mg, from about 30 to about 50 mg, from about 30 to about 40 mg, from about 40 to about 100 mg, from about 40 to about 90 mg, from about 40 to about 80 mg, from about 40 to about 70 mg, from about 40 to about 60 mg, from about 40 to about 50 mg, from about 50 to about 100 mg, from about 50 to about 90 mg, from about 50 to about 80 mg, from about 50 to about 70 mg, from about 50 to about 60 mg, from about 60 to about 100 mg, from about 60 to about 90 mg, from about 60 to about 80 mg, from about 60 to about 70 mg, from about 70 to about 100 mg, from about 70 to about 90 mg, from about 70 to about 80 mg, from about 80 to about 100 mg, from about 80 to about 90 mg, or from about 90 to about 100 mg.

In some embodiments, the composition comprises an opioid antagonist.

In some embodiments, the compositions described herein are a dosage form. A dosage form is where each of the active ingredients or components are mixed together prior to administration. Examples of dosage forms are described herein and include, but are not limited to, pills, capsule, liquid, tablet, and the like. The dosage form can have the same components as discussed herein for the compositions. The ratios of the components can also be the same. In some embodiments, the dosage form is suitable for oral administration or parenteral administration. The composition can also be administered sublingually, bucally, intranasal, and the like.

As discussed herein, in some embodiments, the oral dosage form can comprise an opioid antagonist. In some embodiments, the oral dosage form comprises a sequestered opioid antagonist. A sequestered opioid antagonist is one that is not bioavailable unless the oral dosage form is tampered with or adulterated. Opioids can be abused for their euphoric effect and if the dosage form is a controlled release or sustained release dosage form, crushing the dosage form can increase the bioavailability of the opioid agonist. Therefore, to prevent abuse, the dosage form can be made with the opioid antagonist such that the activity of opioid agonist is inhibited if the dosage form is altered, adulterated or tampered with by the subject using the dosage form. Therefore, in some embodiments, the oral dosage form further comprises a sequestered opioid antagonist which is not released when the dosage form is administered intact. In some embodiments, the sequestered opioid antagonist is in an amount which will negate the euphoric effect of the opioid agonist when the dosage form is tampered with and misused by a human. The form can be misused by administering the tampered dosage form orally, parenterally, intranasally or sublingually. In some embodiments, the sequestered antagonist is selected from the group consisting of naltrexone, naloxone, nalmefene, cyclazocine, levallorphan, pharmaceutically acceptable salts thereof and mixtures thereof. Other examples of sequestered antagonists and formulations thereof are described in U.S. Pat. No. 8,231,901, which is hereby incorporated by reference.

Also provided herein are methods of treating or preventing pain comprising administering to a subject a composition or pharmaceutical composition described herein. In some embodiments, the composition or pharmaceutical composition is administered every 4 hours, every 6 hours, every 8 hours, or every 12 hours. The compositions described herein can be administered by any suitable method. Examples of suitable methods of administration include, but are not limited to, orally, parenteral or topical. Thus, the composition may be, for example, administered subcutaneously, intramuscularly, intravenously, nasally, transdermally or vaginally.

Due to the potential for abuse, many opioids are administered in conjunction with a risk evaluation mitigation strategy (REMS). A REMS can include a medication guide, patient package insert, a communication plan, elements to assure safe use, an implementation system, or any combination thereof. Because the compositions described herein may use less amounts of the opioid agonist, risk evaluation mitigation strategies may not need to be used. Therefore, in some embodiments, the method does not comprise the use of a risk evaluation mitigation strategy or any element of a REMS, some of which are described herein.

In some embodiments, in addition to the components described herein, the composition can comprise non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable agents that can be used include, but not limited to, the following chemical classes of analgesic, antipyretic, non-steroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, Analgesic Antipyretic and Antiinflammatory Agents and Drugs Employed in the Treatment of Gout, in Goodman & Gilman's The Pharmacological Basis of Therapeutics 617-57 (Perry B. Molinhoff and Raymond W. Ruddon eds., 9th ed 1996) and Glen R. Hanson, Analgesic, Antipyretic and Anti Inflammatory Drugs in Remington: The Science and Practice of Pharmacy Vol II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839. Cox II inhibitors include, but are not limited to, rofecoxib and celecoxib.

The compositions described herein can also comprise antimigraine agents, which include but are not limited to, alpiropride, dihydroergotamine, dolasetron, ergocornine, ergocorninine, ergocryptine, ergot, ergotamine, flumedroxone acetate, fonazine, lisuride, lomerizine, methysergide oxetorone, pizotyline, and mixtures thereof.

The pain treated or prevented in accordance with the methods described herein can be acute pain or chronic pain, such as, but not limited to, nociceptive pain, neuropathic pain and psychogenic pain, and can be cancer related or not associated with cancer. Example of "nociceptive pain" include, but are not limited to, pain caused by injury to body tissues, including, without limitation, by a cut, bruise, bone fracture, crush injury, burn, surgery, and the like. In some embodiments, the pain is somatic pain. The term "somatic pain" is used to refer to pain arising from bone, joint, muscle, skin, or connective tissue. This type of pain is typically aching or throbbing in quality and is well localized. The term "neuropathic pain" is used herein to refer to pain originating from abnormal processing of sensory input by the peripheral or central nervous system. The compositions described herein can be used, in some embodiments, to treat or prevent these types of pain.

The compositions described herein can also be administered in a therapeutically effective amount to treat or prevent pain. In some embodiments, none of the components of a pharmaceutical composition are administered to the subject to avoid withdrawal symptoms. Opioids and/or other pain medications can be addictive. Thus, as medications are changed the subject may be weaned off of a medication to avoid withdrawal symptoms. In some embodiments, for the compositions described herein, the different components are administered to treat or prevent pain and not for the purpose of avoiding and/or treating withdrawal symptoms.

In some embodiments, the compositions can be administered to a subject, animal, patient, or mammal in need thereof. As used herein, the phrase "in need thereof" means that the animal, subject, patient or mammal has been identified as having a need for the particular method, use, or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, the term "mammal" means a rodent (i.e., a mouse, a rat, or a guinea pig), a monkey, a cat, a dog, a cow, a horse, a pig, or a human. In some embodiments, the mammal is a human. The methods and uses described herein can be used with any mammal, including a human.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the terms "a" or "an" means that "at least one" or "one or more" unless the context clearly indicates otherwise.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

By "pharmaceutical formulation" or "pharmaceutical composition" it is further meant that the carrier, solvent, excipients and salt must be compatible with the active ingredient of the formulation (e.g. a compound described herein). It is understood by those of ordinary skill in this art that the terms "pharmaceutical formulation" and "pharmaceutical composition" are generally interchangeable, and they are so used for the purposes of this application. As discussed herein, the composition described herein can be a pharmaceutical composition. The composition can also have a pharmaceutically acceptable salt of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic. The present disclosure includes pharmaceutically acceptable salts of any compound(s) described herein.

Pharmaceutically acceptable salts can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile, and the like. Lists of suitable salts are found in Remington's Pharmaceutical Sciences, 18th ed., Mack Publishing Company, Easton, Pa., USA, p. 1445 (1990).

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" includes any effect e.g., lessening, reducing, modulating, or eliminating, that results in the improvement of the condition, disease, disorder, etc. "Treating" or "treatment" of a disease state means the treatment of a disease-state in a mammal, particularly in a human, and include: (a) inhibiting an existing disease-state, i.e., arresting its development or its clinical symptoms; and/or (c) relieving the disease-state, i.e., causing regression of the disease state. With regards to pain, the treatment of pain would be the reduction in the pain sensation that one would have in the absence of the composition being administered. For example, in some embodiments, the terms "treatment of" and "treating" pain include the lessening of the severity of or cessation of pain. In some embodiments, it refers to decreasing the overall frequency of episodes of pain.

As used herein, "preventing" means causing the clinical symptoms of the disease state not to develop i.e., inhibiting the onset of disease, in a subject that may be exposed to or predisposed to the disease state, but does not yet experience or display symptoms of the disease state. Preventing pain may also refer to a subject not having as great of a pain sensation as the subject would have had had the composition not been administered.

As used herein, "mammal" refers to human and non-human patients.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment. The compositions can also be administered in a therapeutically effective amount.

The present compositions can optionally comprise a suitable amount of a pharmaceutically acceptable excipient so as to provide the form for proper administration to the animal. Such pharmaceutical excipients can be, but not limited to, liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can, for example, take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in Remington's Pharmaceutical Sciences 1447-1676 (Alfonso R. Gennaro ed., 19th ed. 1995), incorporated herein by reference.

The compositions described herein can also be formulated to be a controlled- or sustained-release pharmaceutical compositions. Advantages of controlled- or sustained-release compositions include extended activity of the drug or combination of drugs, reduced dosage frequency, and increased patient compliance. In addition, controlled- or sustained-release compositions can favorably affect the time of onset of action or other characteristics, such as blood levels of the compounds, and can thus reduce the occurrence of adverse side effects.

For example, controlled- or sustained-release compositions can initially release an amount of the composition or component that promptly produces the desired therapeutic or prophylactic effect, and gradually and continually release other amounts of the composition or component to maintain this level of therapeutic or prophylactic effect over an extended period of time. To maintain a constant level of the composition or components, the composition or the individual components can be released from the dosage form at a rate that will replace the amount of composition or individual components being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

All percentages and ratios used herein, unless otherwise indicated, are by weight.

Throughout the description, where compositions are described as having, including, or comprising specific components, or where processes are described as having, including, or comprising specific process steps, it is contemplated that compositions described herein also consist essentially of, or consist of, the recited components, and that the processes described herein also consist essentially of, or consist of, the recited processing steps. Further, it should be understood that the order of steps or order for performing certain actions are immaterial so long as the process remains operable. Moreover, two or more steps or actions can be conducted simultaneously.

As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. Thus, for example, a reference to "a host cell" includes a plurality of such host cells, and a reference to "an antibody" is a reference to one or more antibodies and equivalents thereof known to those skilled in the art, and so forth.

EXAMPLES

The following examples are illustrative, but not limiting, of the methods and compositions described herein. Other suitable modifications and adaptations of the variety of conditions and parameters normally encountered in therapy and that are obvious to those skilled in the art are within the spirit and scope of the compounds and methods described herein.

Example 1: Administration of Quinidine/Morphine/Dextramethorphan Treats Pain

The ability of quinidine (Q) to enhance the analgesic effects of MS:DM and reduce tolerance and dependence of MS and MS:DM in rats is determined. Adult Sprague-Dawly rats are used. All experimental protocols are done at a licensed research facility having an institutional animal care and use committee (IACUC) that conforms to the national institute of health (NIH) office of laboratory animal welfare (OLAW).

Morphine sulfate pentahydrate (MS), Dextramethorphan hydrobromide monohydrate (DM), quinidine (Q), and/or Naloxone hydrochloride are ordered from commercially available suppliers and manufacturers. Each component is administered orally through a rodent feeding tube. Rats exhibiting signs of misfeeding (choking, irritation, and irregular breathing) are assessed following each dose and treated appropriately.

Drug Administration and Pain Protocol

The baseline tail-flick latencies of the rats are be set at 3.5 to 4.5 seconds. To minimize tissue damage, and if no tail-flick occurs after 8 seconds, the light (e.g. heat) source is automatically turned off. The average of three tail-flick trials separated by a 1 min inter trial interval is used to determine the mean baseline latency (BL). The analgesic effects of MS, MS:DM, and MS:DM:Q and the development of tolerance is determined by measuring test (tail-flick) latencies (TL) after drug administration. The data can be expressed as percent of maximal possible analgesic effect (% MPAE) using the equation (% MPAE=$[(TL-BL)/(8-BL)] \times 100$).

Determination of the development of morphine tolerance and physical dependence:

Tolerance to MS in rats is determined using the tail flick pain model, and is measured as the time difference between baseline tail flick latencies and test tail flick latencies after MS, MS:DM, and MS:DM:Q administration. Results of the test are that the tricombination of MS:DM:Q have a statistically significant increase in the tail flick latencies compared to baseline and as compared to MS and MS:DM and no drug administration. Additionally, dependence is determined by observing the three physical characteristics of escape jumping, teeth chattering, and wet-dog shakes for 10-15 minutes duration, following intraperitoneal Naloxone challenge.

Dose Dependency

The dose dependent analgesic effects of MS in rats is determined using an oral administration of a range of MS doses, using the tail flick pain model described above. Tail flick latencies are measured at 1, 2, and 3 hours after oral treatment of MS to determine maximal analgesic effects of MS and $ED_{50}$. The oral MS administration is repeated until tolerance and dependence are achieved. This is done by twice daily dosing of MS at the $ED_{50}$ dose (approximately 30 mg/kg) for 5, 10, and 15 days. Tail flick latencies are measured 90 minutes after each treatment until day 15. After tail flick testing, Naloxone is given IP on days 5, 10, and 15 to one group of rats and signs of withdrawal are observed for 10 minutes after injection. One saline treated group of rats will be used as control for all time points.

Escape jumping, teeth chattering, and wet-dog shaking are used to assess physical dependence on MS compared to MS:DM, or MS:DM:Q. These observations are determined following naloxone challenge (10 mg/kg, subcutaneously). The frequency of attempted escape jumping from containers housing the individual rats, and the frequency of episodes of teeth chattering, or wet-dog shaking are counted for a duration of 10 min after naloxone challenge.

Effects of MS/DM and MS/DM/Q Combination on Tolerance and Dependence

A therapeutically effective ratio range of combined administration of MS, DM, and Q that prevents or reduces the development of morphine tolerance and dependence.

Three doses of MS (ED90, ED50, and ED30 doses, respectively) are used to determine whether MS/DM/Q ratios are similar in preventing the development of morphine tolerance and dependence induced by different dose levels of MS.

Groups of rats (e.g. n=12 per group) are used. Each group will receive one MS/DM combinations (MS ED90, ED50, and ED30 plus equal amounts of mg/kg DM), DM alone (mg/kg), MS alone (mg/kg), or saline MS ED90-equivalent mg/kg. After the optimal MS tolerance and dependence reducing MS/DM dose is identified, this combination dose is used with a dose range of Q at 1:1:0.1, 1:1:0.5, and 1:1:1 (MS:DM:Q). The results will show that the tri-combination is more effective at reducing pain.

In all combination experiments, baseline tail-flick latencies of each rat is obtained before dosing. Each group of rats receives oral administration of one of the drug combinations or saline twice a day for 30 days. The analgesic effects of MS is examined at 90 min after the oral feeding using the tail-flick test on day, 5, 10, 15 or 30 of the treatment schedule. The choice of this 30-day treatment regimen is dependent on results of the time course experiment. After tail-flick testing on Day 15 or 30, 10 mg/kg naloxone is given intraperitoneally to each rat, and withdrawal signs are observed and recorded for 10 min following injection.

The time course of the DM-mediated increase in the acute analgesic effects of MS and compare it to MS:DM:Q is determined. MS ED30 dose is used in order to avoid maximal analgesic effects of a high MS dose alone. Four groups (n=12/group) of rats each receive a single oral administration of MS alone, a combination of MS and DM, DM alone, or MS:DM:Q (based upon the optimal combination ratio of MS:DM to Q determined above). The tail-flick test is recorded before and every 30 min after drug administration until tail-flick latencies are back to the baseline level.

The experiments will demonstrate the superior and synergistic effects on analgesia of the tri-combination compared to the components alone.

While the compounds described herein have been described with reference to examples, those skilled in the art recognize that various modifications may be made without departing from the spirit and scope thereof.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

What is claimed is:

1. A dosage form for treating pain consisting of:
   dextromethorphan, or a pharmaceutically acceptable salt thereof;
   quinidine, or a pharmaceutically acceptable salt thereof; and
   morphine, or a pharmaceutically acceptable salt thereof,
   wherein the ratio of dextromethorphan, or a pharmaceutically acceptable salt thereof, to quinidine, or a pharmaceutically acceptable salt thereof; to morphine or a pharmaceutically acceptable salt thereof is about 1:1:1.

2. The dosage form of claim 1, wherein the morphine is morphine sulfate.

3. The dosage form of claim 1, wherein the composition comprises about 10 mg, about 20 mg, about 30 mg, about 40 mg, about 50 mg, or about 60 mg of morphine, or a pharmaceutically acceptable salt thereof.

4. The dosage form of claim 1, wherein said dosage form is an oral dosage form.

5. A method of treating or preventing pain in a subject comprising administering to the subject a pharmaceutical dosage form of claim 1.

6. The dosage form of claim 1, wherein the morphine is morphine hydrochloride or morphine tartrate.

7. A dosage form for treating pain consisting essentially of:
   dextromethorphan, or a pharmaceutically acceptable salt thereof;
   quinidine, or a pharmaceutically acceptable salt thereof; and
   morphine or a pharmaceutically acceptable salt thereof,
   wherein the ratio of dextromethorphan, or a pharmaceutically acceptable salt thereof, to quinidine, or a pharmaceutically acceptable salt thereof; to morphine or a pharmaceutically acceptable salt thereof is about 1:1:1.

8. A method of treating or preventing pain in a subject comprising administering to the subject a pharmaceutical dosage form of claim 7.

9. A dosage form for treating pain comprising:
   active ingredients, wherein the active ingredients consist of:
   dextromethorphan, or a pharmaceutically acceptable salt thereof;
   quinidine, or a pharmaceutically acceptable salt thereof; and
   morphine, or a pharmaceutically acceptable salt thereof,
   wherein the dextromethorphan, or a pharmaceutically acceptable salt thereof to quinidine, or a pharmaceutically acceptable salt thereof to morphine, or a pharmaceutically acceptable salt thereof is about 1:1:1,
   and pharmaceutical acceptable excipients.

10. The dosage form of claim 9, wherein the composition comprises about 10 mg, about 20 mg, about 30 mg, about 40 mg, about 50 mg, or about 60 mg of morphine, or a pharmaceutically acceptable salt thereof.

11. The dosage form of claim 9, wherein the morphine is morphine sulfate.

12. The dosage form of claim 9, wherein the morphine is morphine hydrochloride or morphine tartrate.

13. The dosage form of claim 9, wherein said dosage form is an oral dosage form.

14. The dosage form of claim 7, wherein the composition comprises about 10 mg, about 20 mg, about 30 mg, about 40 mg, about 50 mg, or about 60 mg of morphine, or a pharmaceutically acceptable salt thereof.

15. The dosage form of claim 7, wherein the morphine is morphine sulfate.

16. The dosage form of claim 7, wherein the morphine is morphine hydrochloride or morphine tartrate.

17. The dosage form of claim 7, wherein said dosage form is an oral dosage form.

18. A method of treating or preventing pain in a subject comprising administering to the subject a pharmaceutical dosage form of claim 9.

19. A method of treating or preventing pain in a subject comprising administering to the subject a pharmaceutical dosage form of claim 11.

20. A method of treating or preventing pain in a subject comprising administering to the subject a pharmaceutical dosage form of claim 13.

* * * * *